(12) United States Patent
Shen et al.

(10) Patent No.: US 8,846,968 B2
(45) Date of Patent: Sep. 30, 2014

(54) INTERMEDIATE OF LYCOPENE AND PREPARATION METHOD OF INTERMEDIATE THEREOF

(71) Applicants: ZheJiang Medicine Co., Ltd. Xinchang Pharmaceutical Factory, Xinchang County (CN); Shaoxing University, Xinchang County (CN)

(72) Inventors: Runpu Shen, Xinchang County (CN); Chunlei Lv, Xinchang County (CN); Xiaoyue Jiang, Xinchang County (CN); Xuejun Lao, Xinchang County (CN); Weidong Ye, Xinchang County (CN); Luo Liu, Xinchang County (CN); Xiaohua Song, Xinchang County (CN); Chunlei Wu, Xinchang County (CN)

(73) Assignees: Shaoxing University (CN); Zhejiang Medicine Co., Ltd. Xinchang Pharmaceutical Factory (CN)

( * ) Notice: Subject to any disclaimer, the term of this patent is extended or adjusted under 35 U.S.C. 154(b) by 0 days.

(21) Appl. No.: 13/692,694

(22) Filed: Dec. 3, 2012

(65) Prior Publication Data

US 2014/0005434 A1  Jan. 2, 2014

Related U.S. Application Data

(63) Continuation of application No. PCT/CN2011/000155, filed on Jan. 30, 2011.

(51) Int. Cl.
*C07C 43/303* (2006.01)
*C07F 9/40* (2006.01)
*C07B 47/00* (2006.01)
*C07C 41/50* (2006.01)
*C07C 41/48* (2006.01)

(52) U.S. Cl.
CPC ............... *C07C 41/50* (2013.01); *C07F 9/4015* (2013.01); *C07C 43/303* (2013.01); *C07F 9/4078* (2013.01); *C07B 47/00* (2013.01); *C07C 41/48* (2013.01)
USPC .......................................... 558/186; 568/596

(58) Field of Classification Search
USPC .................... 558/186, 142; 568/596
See application file for complete search history.

(56) References Cited

U.S. PATENT DOCUMENTS 3,962,283 A * 6/1976 Bertele et al. ................. 549/347
7,022,665 B2 * 4/2006 Decorzant et al. ............. 512/25

OTHER PUBLICATIONS

Copending U.S. Appl. No. 13/692,658—published on Jan. 2, 2014.*
Connolly et al. (J. Org. Chem. 1985, (50(21); p. 4135-4144).*

* cited by examiner

*Primary Examiner* — Kristin Vajda
*Assistant Examiner* — Valerie Rodriguez-Garcia
(74) *Attorney, Agent, or Firm* — Daniel A. Thomson; Emerson Thomson Bennett, LLC

(57) ABSTRACT

The present invention relates to an intermediate (12) of lycopene of 2,6,10-trimethyl-1,1-dialkoxyl-3,5,9-undecantriene of formula, (12) and its intermediate of 4-methyl-5,5-dialkoxyl-1-pentenyl-1-phosphonic acid dialkyl ester of formula (10), and their preparation methods. The process route is simple, the starting materials are available easily, the cost is low, and it is valuable in industry.

4 Claims, No Drawings

INTERMEDIATE OF LYCOPENE AND PREPARATION METHOD OF INTERMEDIATE THEREOF

FIELD OF INVENTION

This present invention relates to a method of preparing an intermediate of lycopene of 2,6,10-trimethyl-1,1-dialkoxyl-3,5,9-undecan-triene of formula, (12) and its intermediate of 4-methyl-5,5-dialkoxyl-1-pentenyl-1-phosphonic acid dialkyl ester of formula (10), and their preparation methods.

BACKGROUND OF THE INVENTION

There are approximately 600 kinds of carotenoids naturally, but only six kinds of these have so far been produced industrially such as production by Roche Corporation and BASF Corporation. Lycopene as an important product has important functions on scavenging free radical, antiageing, inhibiting tumor, treating heart attack and so on (H. Gerster, J., Am. Coll. Nutr. 1997, 16, 109; Nutr. Cancer 1995, 24.257; E. Giovannucci. et al. J. Natl. Cancer Inst. 1995, 87, 1767; Chem. Abstracts 1990, 112 91375w), and is widely used for medicines, food additives, feed additives. Roche Corporation develops a synthesis route by the Witting Reaction, wherein it uses expensive and poisonous raw materials such as tri-phenyl phosphorous (K. Meyer, et al., Helv. Chim. Acta 1992, 75.1848). Other former synthesis methods use tri-phenyl phosphorous either (P. Karrer, et al., Helv. Chim. Acta 1950, 33, 1349; B. C. L. Weedon, et al., J. Chem. Soc. 1965, 2019; K. Bernhard and H. Mayer, Pure & Appl.-them. 1991,63, 35).

It has been reported from Publication No. WO 0031086, (2000-06-02) of PCT application that Babler J. H. et al. developed a new method of synthesizing lycopene by the Wittig-Horner Reaction, wherein 3,7,11-trimethyl-2,4,6,10-dodecatetraenyl phosphonic acid diethyl ester of formula (5) as a crucial intermediate undergoes a condensation reaction with decyl di-aldehyde (8) by catalysis of bases for preparing lycopene, the whole synthesis sequence is described as follows.

Firstly, pseudoionone (2) reacts with ethynyl anion to produce tertiary alcohol (7) (3,7,11-trimethyl-4,6,10-dodecatrien-1-yn-3-ol):

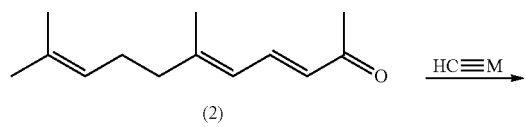

(2)

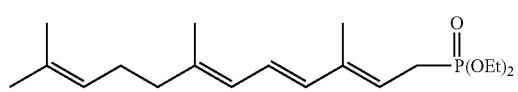

(5)

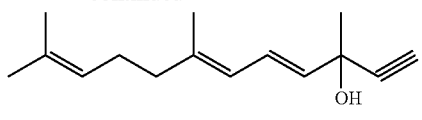

(7)

Afterwards, tertiary alcohol (7) reacts with dialkyl chlorophosphite to produce propadiene pentadecyl phosphoric acid ester (6) (3,7,11-trimethyl-1,2,4,6,10-dodecapentaenyl phosphoric acid diethyl ester).

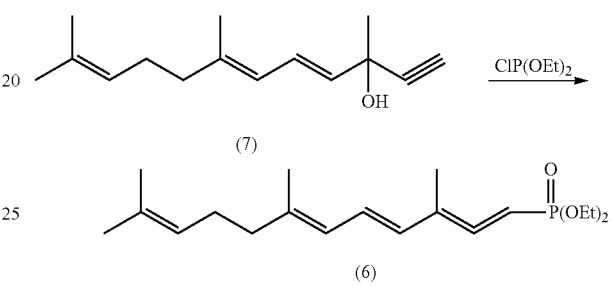

Secondly, propadiene pentadecyl phosphoric acid ester (6) is partially reduced and transformed to pentadecyl phosphoric acid ester (5) (3,7,11-,trimethyl-2,4,6,10-dodecatetraenyl phosphoric acid diethyl ester):

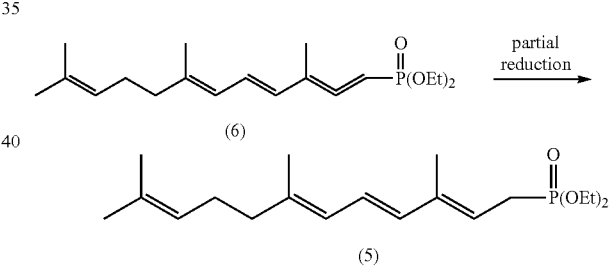

Finally, pentadecyl phosphoric acid ester (5) undergoes a condensation reaction with decanal di-aldehyde (8) (2,7-dimenthyl-2,4,6-octatriene-1,8-dial) by catalysis of bases to obtain lycopene (1).

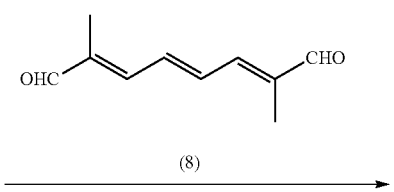

(8)

-continued

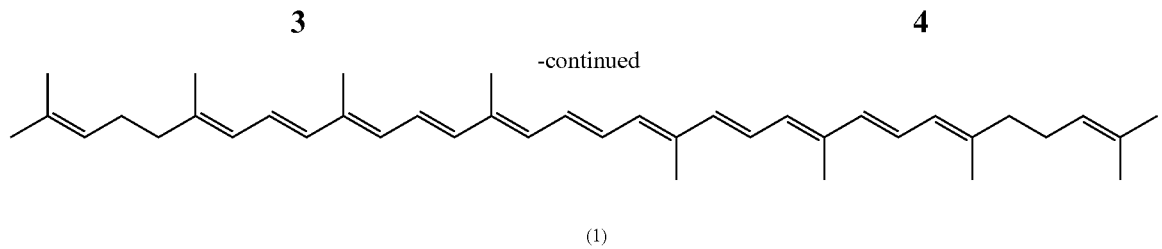

(1)

The method uses a new compound 2,4,6,10-pentadecatetraenyl phosphoric acid ester (5) as an intermediate to avoid uses of triphenyl phosphorous; and moreover uses pseudoionone as a raw material to obtain products of lycopene by reactions of four steps. The synthesis route thereof is concise, and has prominent improvement relative to former methods. However there are some problems in the method. Firstly it is difficulty for reactions of tertiary alcohol (7) with dialkyl chlorophosphite to produce propadiene pentadecyl phosphoric acid ester (6). Secondly it is hard to handle the reduction technology of propadiene pentadecyl phosphoric acid ester (6) selectively being reduced to pentadecyl phosphoric acid ester (5).

Recently, the Chinese patent application No. 2010101042817 of Runbo SHEN et. al. discloses a method of preparing lycopene (1) by a condensation reaction of Wittig-Horner between 1,4,6,10-tetra-double bond pentadec-carbon phosphonate of formula (4) (3,7,11-,trimethyl-1,4,6,10-dodecatetraenyl phosphoric acid diethyl ester) and decanal di-aldehyde (8). The synthesis route of the method comprises the following reaction sequence:

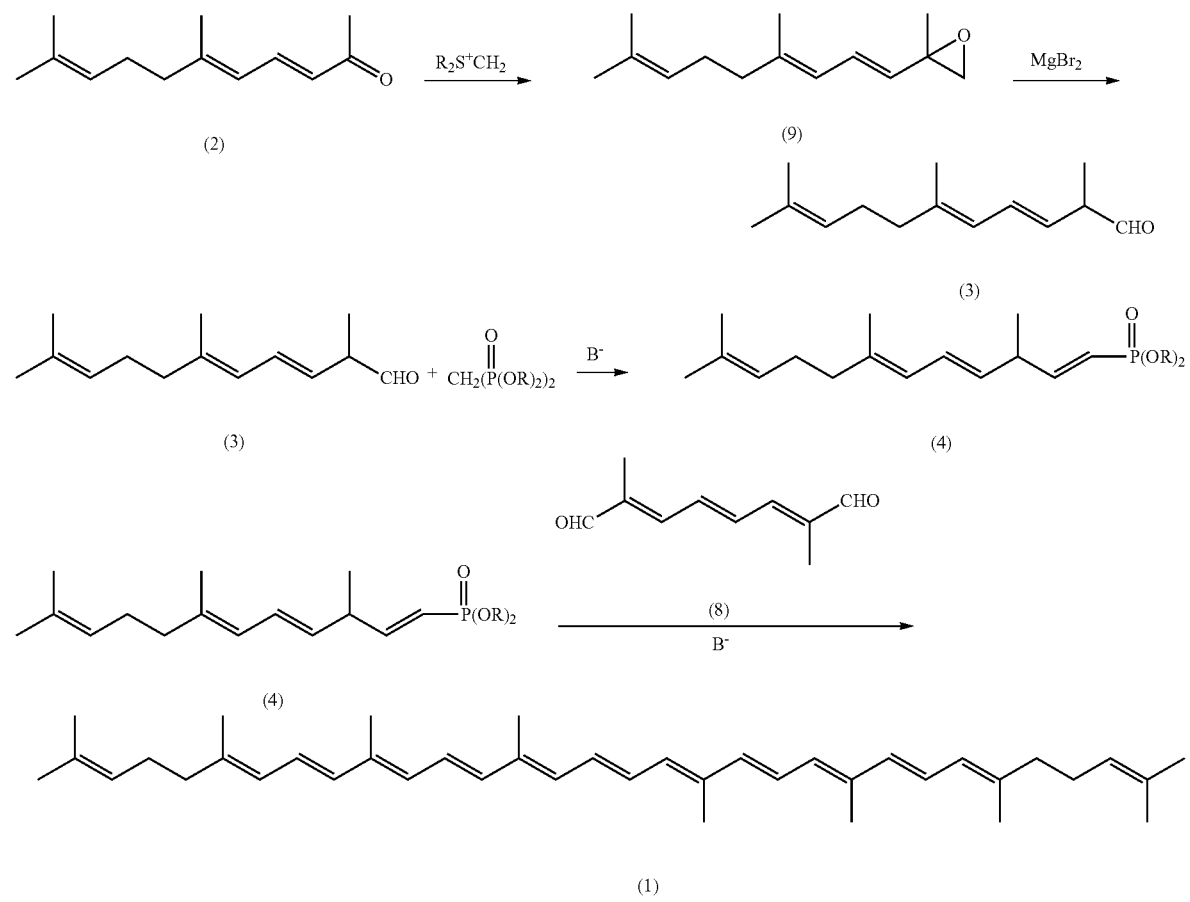

The method of preparing the key intermediate C-14, aldehyde[2,6,10-trimethyl-3,5,9-undecatrienyl-1-aldehyde of formula (3)] refers to the U.S. Pat. No. 4,000,131 (Rosenberger, et al., Oct. 28, 1976). That is, 2,6,10-trimethyl-3,5,9-undecatrienyl-1-aldehyde of formula (3) is obtained by reaction of pseudoionone (2) reacts with sulfonium salt to produce epoxide, and then the epoxide is catalyzed to open a loop to obtain 3-position double bond of formula (3), 2,6,10-trimethyl-3,5,9-undecatrienyl-1-aldehyde. However this method has deficiencies of expensive iodomethane, polluted dimethyl sulfide and dangerous DMSO sodium, and is difficult to apply for industrial production.

SUMMARY OF THE INVENTION

In order to overcome these deficiencies in the prior art, the first objective of the present invention is to provide an intermediate of lycopene, 4-methyl-5,5-dialkoxy-1-pentenyl-1-phosphoric acid dialkyl ester of formula (10):

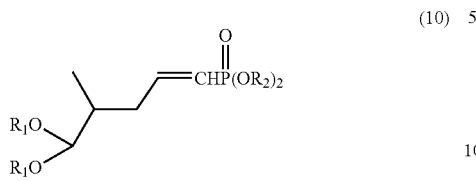

wherein $R_1$ and $R_2$ are $C_{1-4}$ alkyl.

The second objective of the present invention is to provide a method of preparing 4-methyl-5,5-dialkoxy-1-pentenyl-1-phosphoric acid dialkyl ester of formula (10). The method comprises the following steps: undergoing a Wittig-Horner condensation reaction of 3-methyl-4,4-dialkoxy-1-aldehyde of formula(11) with tetra-alkyl methylene diphosphonate at temperature of 0~30° C. in ether solvent or dipolar aprotic solvent and under protection of inert gases in the presence of bases to produce 4-methyl-5,5-dialkoxy -1-pentenyl-1-phosphoric acid dialkyl ester of formula (10). The reaction sequence is described as follows:

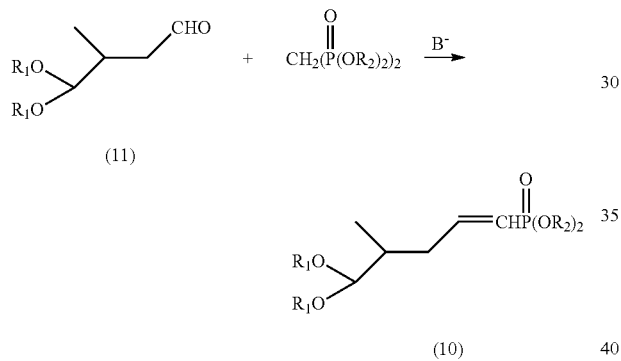

wherein $R_1$ and $R_2$ are $C_{1-4}$ alkyl.

The third objective of the present invention is to provide another intermediate of lycopene, 2,6,10-trimethyl-1,1-dialkoxy-3,5,9-undecan-triene of formula (12):

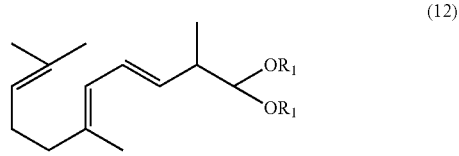

wherein $R_1$ is $C_{1-4}$ alkyl.

The fourth purpose of the present invention is to provide a method of preparing 2,6,10-trimethyl-1,1-dialkoxy-3,5,9-undecan-triene of formula (12). The method comprises the following steps:

Step (1): undergoing a rearrangement reaction and dissociation of 4-methyl-5,5-dialkoxy-1-pentenyl-1-phosphoric acid dialkyl ester of formula (10) at temperature of −40~30° C. in ether solvent or dipolar aprotic solvent and under protection of inert gas in the presence of bases;

Step (2): adding 6-methyl-5-heptene-2-one of formula (13) and undergoing a Wittig-Horner condensation reaction at temperature of −40~30° C. in ether solvent or dipolar aprotic solvent and in the presence of bases to produce 2,6,10-trimethyl-1,1-dialkoxy-3,5,9-undecantriene of formula (12). The reaction sequence is described as follows:

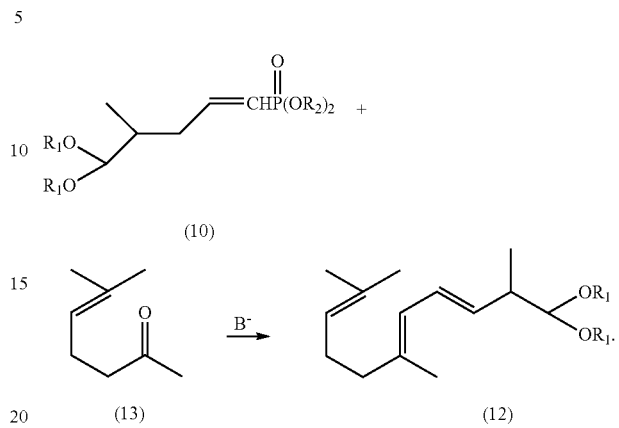

The fifth objective of the present invention is to provide an intermediate of lycopene, 4-methyl-5,5-dialkoxy-1-pentenyl-1-phosphoric acid dialkyl ester of formula (10):

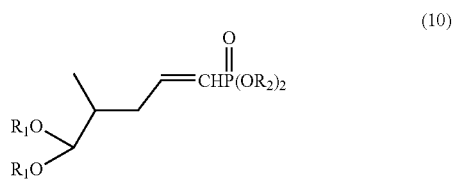

wherein $R_1$ and $R_2$ are $C_{1-4}$ alkyl.

The sixth objective of the present invention is to provide a method of preparing 4-methyl-5,5-dialkoxy-1-pentenyl-1-phosphoric acid dialkyl ester of formula (10). The method comprises the following steps: undergoing a Wittig-Horner condensation reaction of 3-methyl-4,4-dialkoxy-1-aldehyde of formula (11) with tetra-alkyl methylene diphosphonate at temperature of 0~30° C. and in ether solvent or dipolar aprotic solvent and under protection of inert gases in the presence of bases to produce 4-methyl-5,5-dialkoxy -1-pentenyl-1-phosphoric acid dialkyl ester of formula (10). The reaction sequence is described as follows:

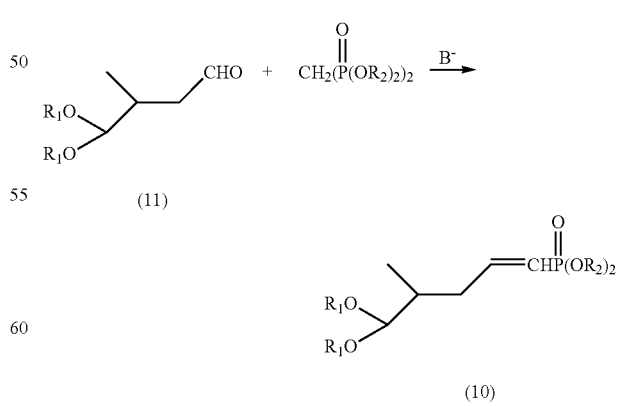

wherein $R_1$ and $R_2$ are $C_{1-4}$ alkyl.

Therefore, 2,6,10-trimethyl-3,5,9-undeca-trienyl-1-aldehyde of formula (3) can be prepared by 2,6,10-trimethyl-1,1- dialkoxy-3,5,9-undecan-triene of formula (12) of the present invention, the preparation method has been described in another application at the same filing date.

The purpose of the present invention is achieved in the cases of overcoming limited reaction conditions of preparing lycopene as well as deficiencies of expensive iodomethane, and contaminated dimethyl sulfide and dangerous DMSO sodium of preparing intermediates of lycopene, 2,6,10-trimethyl-3,5,9-undecatrienyl-1-aldehyde of formula (3).

According to the first aspect of the present invention, it provides compounds of 2,6,10-trimethyl-1,1-dialkoxy-3,5,9-undecan-triene of formula (12):

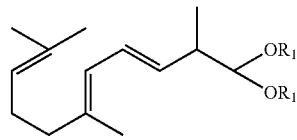

(12)

wherein R$_1$ is C$_{1-4}$ alkyl;
wherein, the 2,6,10-trimethyl-1,1-dialkoxy-3,5,9-undecan-triene is 2,6,10-trimethyl-1,1-dimethoxy-3,5,9-undecan-triene.

According to the second aspect of the present invention, it provides a method of preparing 2,6,10-trimethyl-1,1-dialkoxy-3,5,9-undecan-triene of formula (12), the method comprises the following steps:

Step (1): 4-methyl-5,5-dialkoxy-1-pentenyl-1-phosphoric acid dialkyl ester of formula (10) undergoes a rearrangement reaction at temperature of −40~30° C. in ether solvent or dipolar aprotic solvent and under protection of inert gas in the presence of bases; the reaction sequence is described as follows:

Step (2): 6-methyl-5-heptene-2-one of formula (13) is added to the product of Step (1) to undergo a Wittig-Horner condensation reaction at a temperature of −40~30° C. in ether solvent or dipolar aprotic solvent and in the presence of bases to produce 2,6,10-trimethyl-1,1-dialkoxy-3,5,9-undecan-triene of formula (12). The reaction sequence of Step 11-2 is described as follows:

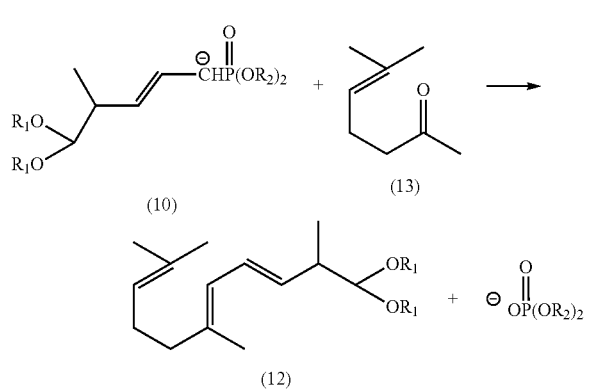

In particular, in Step (1), 4-methyl-5,5-dialkoxy-1-pentenyl-1-phosphoric acid dialkyl ester of formula (10) undergoes a rearrangement reaction and dissociation at temperature of −40~30° C. in ether solvent or dipolar aprotic solvent and under protection of inert gas in the presence of bases to produce a rearrangement product with a carbanion of formula (10A). It is found by tracking gas chromatography that 4-methyl-5,5-dialkoxy-1-pentenyl-1-phosphoric acid dialkyl ester of formula (10) fully rearranges to a carbanion of formula (10A). The rearrangement product is double bond, cis-trans isomers. The reaction sequence of the step is described as follows:

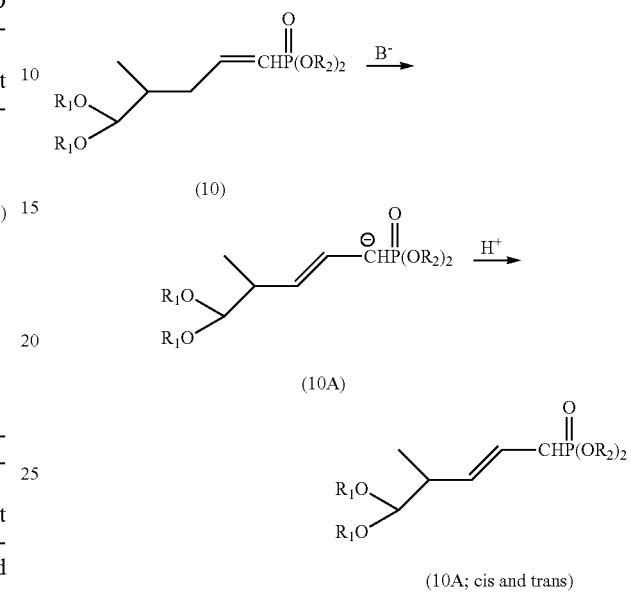

Step (2-2): after fully rearrangement reaction and dissociation, 6-methyl-5-heptene-2-one of formula (13) is added to under go a Wittig-Horner condensation reaction to produce 2,6,10-trimethyl-1,1-dialkoxy-3,5,9-undecan-triene of formula (12), at temperature of −40~30° C. in ether solvent or dipolar aprotic solvent and in the presence of bases. It is essentially a condensation reaction between the carbanion of formula (10A) and 6-methyl-5-heptenyl-2-one of formula (13), wherein the by-product is phosphonic acid dialkyl ester salt. The reaction sequence of the Step is described as follows:

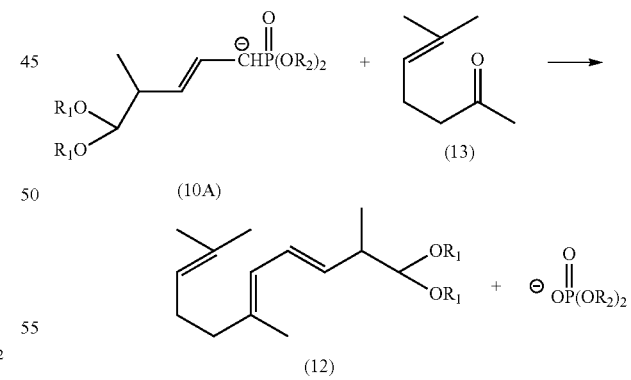

Preferably, a molar ratio of dosage of 4-methyl-5,5-dialkoxy-1-pentenyl-1-phosphoric acid dialkyl ester of formula (10) to the bases is 1:1.0~1.2. A molar ratio of dosage of 4-methyl-5,5-dialkoxy-1-pentenyl-1-phosphoric acid dialkyl ester of formula (10) to 6-methyl-5-heptene-2-one of formula (13) is 1:0~1.2.

More preferably, a molar ratio of dosage of 4-methyl-5,5-dialkoxy-1-pentenyl-1-phosphoric acid dialkyl ester of formula (10) to the bases is 1:1.02~1.1. A molar ratio of dosage of 4-methyl-5,5-dialkoxy-1-pentenyl-1-phosphoric acid dialkyl ester of formula (10) to 6-methyl-5-heptene-2-one of formula (13) is 1:0.9~1.1.

Preferably, the bases comprise alkali metal salt of alcohols and alkyl lithium, wherein the alkali metal salt of alcohols is sodium ethoxide, sodium tert-butoxide or potassium tert-butoxide; the alkyl lithium is butyl lithium. The ether solvent is ether, tetrahydrofuran or ethylene glycol dimethyl ether. The dipolar aprotic solvent is dimethyl formamide, dimethyl sulfoxide or hexamethyl phosphoric triamide. The rearrangement reaction undergoes at a temperature of –20~10° C.

After the end of the condensation reaction, water is added to segregate from organic solvent, the by-product such as phosphoric acid diethyl ester is dissolved in water, the product of 2,6,10-trimethyl-1,1-dialkoxy-3,5,9-undecan-triene of formula (12) is in organic phase, to remove the solvent after evaporation, to obtain the objective product of 2,6,10-trimethyl-1,1-dialkoxy-3,5,9-undecan-triene of formula (12).

According to the third aspect of the invention, it provides 4-methyl-5,5-dialkoxy-1-pentenyl-1-phosphoric acid dialkyl ester of formula (10):

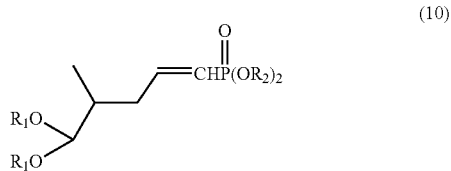

wherein $R_1$ and $R_2$ are $C_{1-4}$ alkyl.

Wherein, the 4-methyl-5,5-dialkoxy-1-pentenyl-1-phosphoric acid dialkyl ester is 4-methyl-5,5-dimethoxy-1-pentenyl-1-phosphoric acid dimethyl ester, 4-methyl-5,5-dimethoxy-1-pentenyl-1-phosphoric acid diethyl ester or 4-methyl-5,5-dimethoxy-1-pentenyl-1-phosphoric acid diisopropyl ester.

According to the fourth aspect of the invention, it provides a method of preparing 4-methyl-5,5-dialkoxy-1-pentenyl-1-phosphoric acid dialkyl ester of formula (10). The method comprises the following steps:

The 3-methyl-4,4-dialkoxy-1-aldehyde of formula (11) undergoes a Wittig-Horner condensation with tetra-alkyl methylene diphosphonate at temperature of 0~30° C. in ether solvent or dipolar aprotic solvent and under protection of inert gases in the presence of bases to produce 4-methyl-5,5-dialkoxy-1-pentenyl-1-phosphoric acid dialkyl ester of formula (10). The reaction sequence is described as follows:

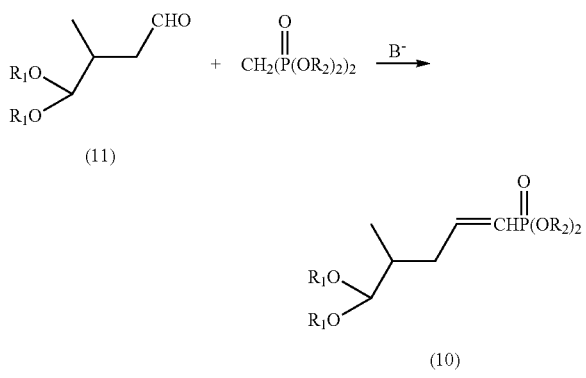

wherein $R_1$ and $R_2$ are $C_{1-4}$ alkyl.

Preferably, the tetra-alkyl methylene diphosphonate is tetra-methyl methylene diphosphonate, tetra-ethyl methylene diphosphonate or tetra-isopropyl methylene diphosphonate.

Preferably, a molar ratio of dosage of the 3-methyl-4,4-dialkoxy-1-aldehyde of formula (11) to the bases is 1:1.0~1.2. A molar ratio of dosage of the 3-methyl-4,4-dialkoxy-1-aldehyde of formula (11) to the tetra-alkyl methylene diphosphonate is 1:1.0~1.3. More preferably, a molar ratio of dosage of the 3-methyl-4,4-dialkoxy-1-aldehyde of formula (11) to the bases is 1:1.02~1.1. A molar ratio of dosage of the 3-methyl-4,4-dialkoxy-1-aldehyde of formula (11) to the tetra-alkyl methylene diphosphonate is 1:1.05~1.15.

Preferably, the bases is alkali metal hydride, alkali metal salt of alcohols and alkyl lithium; wherein the alkali metal hydride is sodium hydride or potassium hydride; the alkali metal salt of alcohols is sodium ethoxide, sodium tert-butoxide or potassium tert-butoxide; the alkyl lithium is butyl lithium. The ether solvent is ether, tetrahydrofuran or ethylene glycol dimethyl ether. The dipolar aprotic solvent is dimethyl formamide, dimethyl sulfoxide or hexamethyl phosphoric triamide.

The condensation reaction undergoes at a temperature of –20~10° C.

Preferably, the tetra-alkyl methylene diphosphonate firstly reacts with the bases to produce a corresponding carbanion, and then 3-methyl-4,4-dialkoxy-1-aldehyde of formula (11) is added to undergo a Wittig-Horner condensation; or tetra-alkyl methylene diphosphonate firstly mixes with 3-methyl-4,4-dialkoxy-1-aldehyde of formula (11) and then is added into the bases.

Finally, the 2,6,10-trimethyl-1,1-dialkoxy-3,5,9-undecan-triene of formula (12) is mixed with acid catalysts, water and homogeneous solvents, and undergoes a hydrolysis reaction at the temperature of 10~35° C. under protection of inert gas to produce 2,6,10-trimethyl-3,5,9-undecatrienyl-1-aldehyde of formula (3). The reaction sequence is described as follows:

In the method of preparing 2,6,10-trimethyl-3,5,9-undecatrienyl-1-aldehyde of formula (3), the reaction raw materials such as 3-methyl-4,4-dialkoxy-1-aldehyde of formula (11), tetra-alkyl methylene diphosphonate and 6-methyl-5-heptene-2-one of formula (13) are provided by Zhejiang Medicine Co., Ltd Xinchang Pharmaceutical Factory. Besides, these compounds may also be prepared by reference documents, for example, 3-methyl-4,4-dialkoxy-1-aldehyde of formula (11) may be prepared according to the method disclosed in U.S. Pat. No. 4,675,451. The reaction sequence is described as follows:

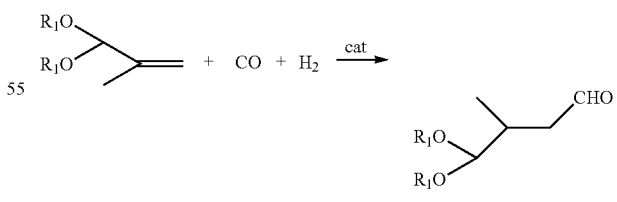

Both of tetra-alkyl methylene diphosphonate and 6-methyl-5-heptene-2-one of formula (13) are obtained from regular industrial raw materials.

As described above, it takes three steps for the present invention to produce the key intermediate of lycopene, 2,6,10-trimethyl-3,5,9-undecatrienyl-1-aldehyde of formula (3) by using 3-methyl-4,4-dialkoxy-1-aldehyde of formula (11)

as raw materials. Hence it takes the advantages of short process route, easy acquisition of raw materials, low cost and high industrial value.

The method of preparing lycopene is also adopted based on the method of the Chinese application No. 2010101042817.

Step (1): 2,6,10-trimethyl-3,5,9-undecatrienyl-1-aldehyde of formula (3) undergoes a Wittig-Horner condensation reaction with tetra-alkyl methylene diphosphonate, at temperature of 0~30° C. in ether solvent or dipolar aprotic solvent and under protection of inert gases in the presence of bases, to produce 1,4,6,10-tetra-double bond pentadec-carbon phosphonate of formula (4). The reaction sequence is described as follows.

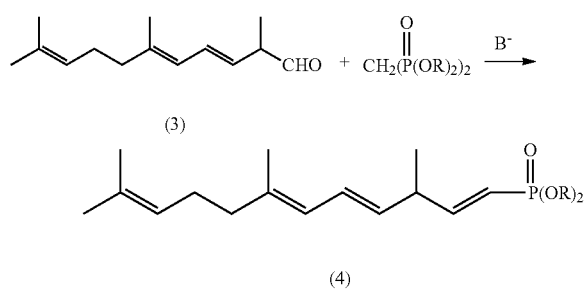

wherein $R_1$ and $R_2$ are $C_{1-4}$ alkyl.

Step (2): 1,4,6,10-tetra-double bond pentadec-carbon phosphonate of formula (4) undergoes a rearrangement reaction at temperature of −40~30° C. in ether solvent or dipolar aprotic solvent and under protection of inert gas in the presence of alkali; and then decyl di-aldehyde of formula (8) is added to undergo a Wittig-Horner condensation reaction to produce lycopene of formula (1) at temperature of −40~30° C. and in ether solvent or dipolar aprotic solvent, under protection of inert gas and in the presence of bases. The reaction sequence is described as follows.

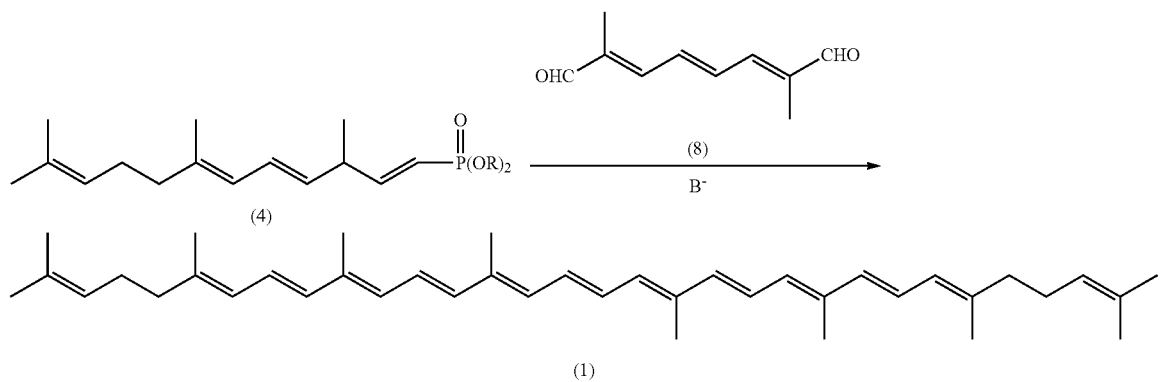

As described above, it takes five steps for the present invention to produce the objective product of lycopene (1) by using 3-methyl-4,4-dialkoxy-1-aldehyde of formula (11) as raw materials. Hence it takes the advantages of short process route, easy acquisition of raw materials, low cost and high industrial value.

Please note that 4-methyl-5,5-dialkoxy-1-pentenyl-1-phosphoric acid dialkyl ester of formula (10) is a single compound verified by tracking gas chromatography and nuclear magnetic resonance. The condensation product of 2,6,10-trimethyl-1,1-dialkoxy-3,5,9-undecan-triene of formula (12) is cis-trans isomeric mixtures. But these cis-isomers of these intermediates do not affect the all-trans structure of the final product-lycopene of formula (1), because the final product of all-trans lycopene are obtained through cis-trans isomerization and purification of the crude product of lycopene

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Apparatuses and devices of Examples of the present invention are as follows: Gas chromatograph-Mass Spectrometer, MS5973N-GC6890N (Agilent Technologies, US); Nuclear Magnetic Resonance Spectrometer, AVANCE DMX II I 400M (TMS as internal standard, Bruker Corporation); infrared spectrometer, NICOLET 360FT-IR; gas chromatograph, Techcomp Corp. 7890F.

EXAMPLE 1

Preparation of 4-methyl-5,5-dimethoxy-1-pentenyl-1-phosphoric acid diethyl ester of Formula (10)

4.4 g of sodium hydride (0.11 mol) (60% content) is added in a 250 ml three necked flask under protection of nitrogen, and washed with 20 ml of hexane for twice to remove paraffin oil from sodium hydride, and then 20 ml of toluene is added into the flask, and then 60 ml of toluene dissolving 34.5 g of tetraethyl methylene diphosphonate (0.12 mol) is dropped into the flask under magnetic stirring at temperature 10~15° C. of cold water bath for half an hour to release a large amount of gas, and continuously stirring for half an hour.

Then 40 ml of toluene dissolving 14.4 g of 3-methyl-4,4-dimethoxy-1-aldehyde of formula (11) (0.1 mol) is dropped into the flask at temperature kept at 10~15° C. of cold water bath for half an hour, and continuously stirring for half an hour to form a mixture.

40 ml of water is added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain 26.2 g crude product of 4-methyl-5,5-dimethoxy-1-pentenyl-1-phosphoric acid diethyl ester of formula (10) with colorless liquid, content of the crude product is 92.2% detected by GC analysis, yield is 86.9%. The crude product is evaporated with a boiling point of 107-111° C./1 mmHg Determination of Product Structure:

GC-MS(m/e): 279, 265, 249, 220, 205, 195, 177, 163, 149, 121, 111, 95, 81, 75(100%), 67, 47, 29;

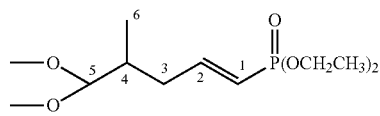

1HNMR($\delta$, ppm, 400 MHz, CDCl3): 0.920(d, J=6.8 Hz, 3H, C6-H); 1.327(t, J=7.2 Hz, 6H, OCH2C*H3); 1.907-1.972 (m, 1H, C4-H); 2.025-2.103, 2.426-2.488 (m, m, 2H, C3-H); 3.339, 3.355(s,s, 6H, (OCH3)2); 4.038-4.109(m, 4H, OC*H2CH3); 4.054(d, J=6.4 Hz,1H, C5-H); 5.674(dd, J=16.8 Hz, 21.6 Hz, 1H, C1-H); 6.696-6.793(m, 1H, C2-H);

13CNMR($\delta$, ppm, 400 MHz, CDCl3): 152.12, 152.07(C2); 119.40, 117.54(C1); 108.11(C5); 61.63, 61.58 (POC*H2CH3); 54.60, 54.01(OCH3); 36.84, 36.62(C3); 35.23(C4); 16.42, 16.35 (OCH2C*H3); 14.45(C6).

EXAMPLE 2

Preparation of
4-methyl-5,5-dimethoxy-1-pentenyl-1-phosphoric
acid dimethyl ester of Formula (10)

4.4 g of sodium hydride (0.11 mol) (60% content) is added in a 250 ml three necked flask under protection of nitrogen, and washed with 20 ml of hexane for twice to remove paraffin oil from sodium hydride, and then 20 ml of toluene is added into the flask, and then 60 ml of toluene dissolving 27.9 g of tetramethyl methylene diphosphonate (0.12 mol) is dropped into the flask under magnetic stirring at temperature 10~15° C. of cold water bath for half an hour to release a large amount of gas, and continuously stirring for half an hour.

Then 40 ml of toluene dissolving 14.4 g of 3-methyl-4,4-dimethoxy-1-aldehyde of formula (11) (0.1 mol) is dropped into the flask at temperature kept at 10~15° C. of cold water bath for half an hour, and continuously stirring for half an hour to form a mixture.

40 ml of water is added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain 25.2 g crude product of 4-methyl-5,5-dialkoxy-1-pentenyl-1-phosphoric acid dimethyl ester of formula (10) with colorless liquid, content of the crude product is 91.7% detected by GC analysis, yield is 91%.

Determination of Product Structure:

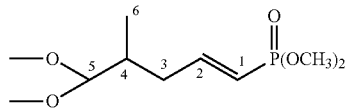

1HNMR($\delta$, ppm, 400 MHz, CDCl3): 0.923(d, J=6.8 Hz, 3H, C6-H); 1.897-1.962(m, 1H, C4-H); 2.038-2.116, 2.417-2.523(m, m, 2H, C3-H); 3.356, 3.367 (s, s, 6H, (OCH3)2); 3.709, 3.736 (m, 6H, OC*H3); 4.057(d, J=6.0 Hz,1H, C5-H); 5.647(dd, J=16.8 Hz, 21.6 Hz, 1H, C1-H); 6.715-6.847(m, 1H, C2-H);

13CNMR ($\delta$, ppm, 400 MHz , CDCl3): 153.27, 153.22 (C2); 117.83,115.97(C1); 108.02(C5); 54.59,53.98(OCH3); 52.28,52.23(POCH3); 36.87, 36.65(C3); 35.14(C4); 14.45 (C6).

EXAMPLE 3

Preparation of
4-methyl-5,5-dimethoxy-1-pentenyl-1-phosphoric
acid diisopropyl ester of Formula (10)

4.4 g of sodium hydride (0.11 mol) (60% content) is added in a 250 ml three necked flask under protection of nitrogen, and washed with 20 ml of hexane for twice to remove paraffin oil from sodium hydride, and then 20 ml of toluene is added into the flask, and then 60 ml of toluene dissolving 41.3 g of tetraisopropyl methylene diphosphonate (0.12 mol) is dropped into the flask under magnetic stirring at temperature 10~15° C. of cold water bath for half an hour to release a large amount of gas, and continuously stirring for half an hour.

Then 40 ml of toluene dissolving 14.4 g of 3-methyl-4,4-dimethoxy-1-aldehyde of formula (11) (0.1 mol) is dropped into the flask at temperature kept at 10-15° C. of cold water bath for half an hour, and continuously stirring for half an hour to form a mixture.

40 ml of water is added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain 29.3 g crude product of 4-methyl-5,5-dimethoxy-1-pentenyl-1-phosphoric acid diisopropyl ester of formula (10) with colorless liquid, content of the crude product is 92.5% detected by GC analysis, yield is 89.7%.

Determination of Product Structure:

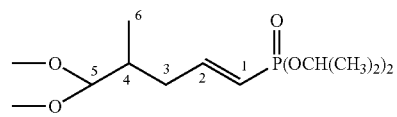

$^1$HNMR($\delta$, ppm, 400 MHz, CDCl$_3$): 0.914(d, J=6.4 Hz,3H, C6-H); 1.327-1.365(m, 12H, OCH(C*H$_3$)$_2$); 1.903-1.986(m, 1H, C4-H); 2.025-2.082, 2.325-2.456(m, m, 2H, C3-H); 1.608, 3.363, 3.354(s, s, s, 6H, (OCH$_3$)$_2$); 4.055(d, J=6.0 Hz, 1H, C5-H); 4.735-4.814(m, 2H, OC*H(CH$_3$)$_2$); 5.682(dd, J=17.2 Hz, 20.8 Hz, 1H, C1-H); 6.645-6.734(m, 1H, C2-H);

$^{13}$CNMR($\delta$, ppm,400 MHz, CDCl$_3$): 150.85,150.80(C2); 121.01,119.15(C1); 108.00(C5); 71.14,71.11,71.08 (OC*H (CH$_3$)$_2$); 54.48, 53.93(OCH$_3$); 36.70,36.47(C3); 35.15(C4); 23.91, 23.95, 24.02, 24.06 (OCH(C*H$_3$)$_2$); 14.34(C6).

EXAMPLE 4-10

Preparation of 4-methyl-5,5-dimethoxy-1-pentenyl-1-phosphoric acid diethyl ester of Formula (10) by a Condensation Reaction in Conditions of Different Alkali, Different Solvent and Different Temperature Using the same method as Example 1, a certain amount of alkali and solvent (refer to Table 1) are added into a 250 ml three necked flask under protection of nitrogen, and 40 ml solvent (refer to solvent of Table 1) dissolving a certain amount of tetraethyl methylene diphosphonate (refer to molar weight of Table 1) is dropped into the flask under magnetic stirring at temperature 10~15° C. of cold water bath for half an hour to release a large amount of gas, and continuously stirring for 20 minutes.

Then 20 ml solvent (refer to solvent of Table 1) dissolving 5.8 g of 3-methyl-4,4-dimethoxy-1-aldehyde of formula (11) (0.040 mol) is dropped into the flask at temperature kept at certain temperature (refer to temperature of Table 1) for half an hour, and continuously stirring for 20 minutes to form a mixture.

40 ml of water and 100 ml ether are added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain crude product of 4-methyl-5, 5-dimethoxy-1-pentenyl-1-phosphoric acid diethyl ester of formula (10) with colorless or faint yellow liquid, used for measuring content of the crude product by GC analysis and yield. Results are shown in Table 1

EXAMPLE 11

Preparation of 2,6,10-trimethyl-1,1-dimethoxy-3,5,9-undecantriene of Formula (12)

6.2 g (0.11 mol) of potassium tert-butoxide and 30 ml mixture of tetrahydrofuran: dimethyl sulfoxide (8:1 (v:v)) are added in a 250 ml a three neck flask in cold water bath under mechanical stirring, under protection of nitrogen, 14.0 g (0.05 mole) of 4-methyl-5,5-dimethoxy-1-pentenyl-1-phosphoric acid diethyl ester of formula (10) is dropped into the flask at temperature of −30~25° C. for half an hour until the end of dropping, continuously stirring under the same temperature for an hour to make a carbanion undergo dissociative reaction fully. At this time the samples are took and a small amount of water is added into the samples for stratification, the organic layer is detected for gas chromatography analysis to confirm 4-methyl-5,5-dimethoxy-1-pentenyl-1-phosphoric acid diethyl ester of formula (10) are fully rearranged to 4-methyl-5,5-dimethoxy-2-pentenyl-1-phosphoric acid diethyl ester of formula (10A), the rearrangement product is a mixture of cis-trans isomers. The reaction sequence of the step is described as follows:

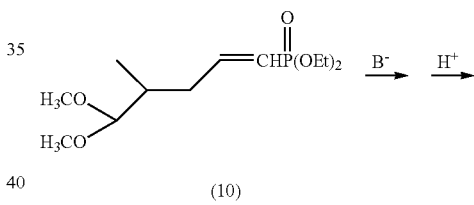

(10)

TABLE 1

Results of Reactants, Reaction Temperatures of Condensation Reaction of Examples 4-10

| Example | Alkali | Amount of alkali (mole) | Solvent | Tetraethyl methylene diphosphonate (mole) | Reaction temperature (°C.) | Amount of Product (g) | GC content (%) | Yield (%) |
|---|---|---|---|---|---|---|---|---|
| 4 | sodium ethoxide | 0.0480 | toluene | 0.0520 | 5 | 10.4 | 93.2 | 87.2 |
| 5 | sodium tert-butoxide | 0.0400 | ethylene glycol dimethyl ether | 0.0400 | 10 | 10.8 | 92.9 | 89.6 |
| 6 | potassium tert-butoxide | 0.0408 | dimethyl formamide | 0.0420 | 20 | 11.2 | 93.1 | 93.8 |
| 7 | n-butyl lithium | 0.0480 | tetrahydro-furan/n-hexane | 0.0520 | 0 | 11.2 | 93.5 | 94.2 |
| 8 | DMSO sodium salt | 0.0420 | DMSO | 0.0432 | 30 | 10.0 | 91.3 | 82.1 |
| 9 | potassium hydride | 0.0412 | toluene | 0.0432 | 20 | 11.2 | 92.5 | 93.2 |
| 10 | sodium methoxide | 0.0440 | ether | 0.0460 | 15 | 8.4 | 89.7 | 73.3 |

Note:
n-butyl lithium is 2.5 mol/l n-hexane solution thereof

Finally combine these crude products obtained to get 73.2 g crude product of 4-methyl-5,5-dimethoxy- 1-pentenyl-1-phosphoric acid diethyl ester of formula (10) used for the following condensation reaction.

-continued

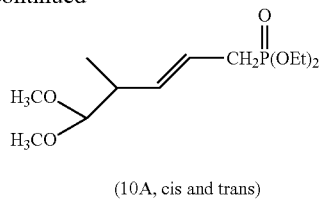

(10A, cis and trans)

Determination of Product Structure:
GC-MS (m/e): 279, 262, 247, 231, 223, 191, 163, 135, 125, 109, 102, 93, 81, 75(100%), 47, 29;

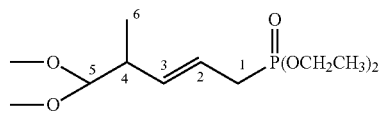

$^1$HNMR($\delta$, ppm, 400 MHz, CDCl$_3$): 0.878-0.967, 0.984-1.046(m, m, 3H, C6-H); 1.319(s, 6H, OCH$_2$C*H$_3$); 1.704-1.750, 1.894-1.956(m, m, 2H, C1-H); 2.450-2.604(m, 1H, C4-H); 3.356(s, 6H, (OCH$_3$)$_2$); 4.001-4.203(m, 4H, OC*H$_2$CH$_3$); 4.016-4.145(m, 1H, C5-H); 5.367-5.506(m, 1H, C2-H); 5.582-5.707(m, 1H, C3-H)
$^{13}$CNMR ($\delta$, ppm, 400 MHz, CDCl$_3$): 136.42, 136.28(C3); 119.26, 119.15(C2); 107.98, 107.82(C5); 61.27, 61.23 (POC*H$_2$CH$_3$); 53.76, 53.73(OCH$_3$); 33.59(C4); 31.25, 30.95(C1); 16.39 (OCH$_2$C*H$_3$); 14.92, 14.72(C6).

Then, 6.3 g of 6-methyl-5-heptene-2-one of formula (13) (0.05 mol) is dropped into the flask at a temperature of −30~25° C. for an hour, continuously stirring for half an hour at the same temperature, and trace the end of the reaction by tracking gas chromatography. 30 ml of water and 60 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residual material is evaporated at reduced pressure, the fraction within 99-103° C./1 mmHg is collected 9.4 g, the fraction is a colorless transparent liquid, the product shows four peaks through GC analysis, the total content is 87.5%, the yield is 65.3%. Four products are respectively 3,4-double bond cis-trans isomers and 5,6-double bond cis-trans isomers.

Verification of Structure of the Product:(Only all Trans Isomers are Listed, Other Cis Isomers are Omitted):
GC-MS (m/e): 252, 220, 192(100%), 178, 165, 152, 115, 102, 91, 77, 65, 51, 39;

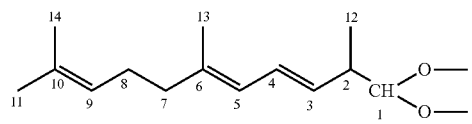

$^1$HNMR($\delta$ppm, 400 MHz, CDCl$_3$): 1.003(d, J=6.8 Hz, 3H, C$_{12}$-H); 1.605(s, 3H, C14-H); 1.679(s, 3H, C$_{11}$-H); 1.745(s, 3H, C$_{13}$-H); 2.036-2.184(m, 4H, C$_7$-H, C$_8$-H); 2.928-2.969 (m, 2H, C$_2$-H); 3.378,3.381(s, s, 6H, (OCH$_3$)$_2$); 4.120-4.144 (m, 1H, C$_1$-H); 5.099-5.130(m, 1H, C$_9$-H); 5.190-5.268(q, J=10.4 Hz, 1H, C$_3$-H); 6.058 (d, J=11.2 Hz, 1H, C$_5$-H); 6.188-6.253(m, 1H, C$_4$-H)

$^{13}$CNMR ($\delta$ppm, 400 MHz, CDCl$_3$): 139.44 (C6); 131.61 (C10); 130.07 (C3); 124.87 (C4); 124.05(C9); 119.76(C5); 108.15(C1); 53.64(OCH$_3$); 40.29 (C7); 35.27 (C2); 26.57 (C8); 25.70 (C11); 17.68 (C12); 16.52(C14); 16.16 (C13);
DEPT135: 139.44; 131.61; 130.07; 124.87; 124.05; 119.76; 108.15; 53.64; 40.29 (D); 35.27; 26.57(D); 25.70; 17.68; 16.52; 16.16;

EXAMPLE 12

Preparation of
2,6,10-trimethyl-1,1-dimethoxy-3,5,9-undecantriene of Formula (12)

6.2 g of potassium tert-butoxide (0.11 mol) and 30 ml mixture of tetrahydrofuran: dimethyl sulfoxide (8:1 (v:v)) are added into a 250 ml a three neck flask in cold water bath under mechanical stirring, under protection of nitrogen, 12.7 g (0.05 mole) of 4-methyl-5,5-dimethoxy-1-pentenyl-1-phosphoric acid dimethyl ester of formula (10) is dropped into the flask at temperature of −30~−25° C. for half an hour, and then continuously stirring under the same temperature for an hour to make a carbanion undergo dissociative reaction fully.

Then, 6.3 g (0.05 mol) of 6-methyl-5-heptene-2-one of formula (13) is dropped into the flask at a temperature of −30~−25° C. for an hour, and continuously stirring for half an hour at the same temperature, and trace the end of the reaction by tracking gas chromatography. 30 ml of water and 60 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residue is evaporated at reduced pressure, the fraction within 99-103° C./1 mmHg is collected 9.4 g, the fraction is a colorless transparent liquid, the product shows four peaks through GC analysis, the total content is 86.7%, the yield is 66.1%. Four products are respectively 3,4-double bond cis-trans isomers and 5,6-double bond cis-trans isomers. Datum of $^1$HNMR of example 12 is the same as that of example 11.

EXAMPLE 13

Preparation of
2,6,10-trimethyl-1,1-dimethoxy-3,5,9-undecantriene of Formula (12)

6.2 g of potassium tert-butoxide (0.11 mol) and 30 ml mixture of tetrahydrofuran: dimethyl sulfoxide (8:1 (v:v)) are added into a 250 ml a three neck flask in cold water bath under mechanical stirring, under protection of nitrogen, 15.1 g (0.05 mole) of 4-methyl-5,5-dimethoxy-1-pentenyl-1-phosphoric acid diisopropyl ester of formula (10) is dropped into the flask at temperature of −30~25° C. for half an hour, and then continuously stirring under the same temperature for an hour to make a carbanion undergo dissociative reaction fully.

Then, 6.3 g (0.05 mol) of 6-methyl-5-heptene-2-one of formula (13) is dropped into the flask at a temperature of −30~25° C. for an hour, and continuously stirring for half an hour at the same temperature, and trace the end of the reaction by tracking gas chromatography. 30 ml of water and 60 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residue is evaporated at reduced pressure, the fraction within 99-103° C./1 mmHg is collected 10.1 g, the fraction is a colorless transparent liquid, the product shows four peaks through GC analysis, the total content is 87.8%, the yield is 70.4%. Four products are respectively 3,4-double bond cis-trans isomers and 5,6-double bond cis-trans isomers. Datum of ¹HNMR of example 12 is the same as that of example 11.

EXAMPLES 14-19

Preparation of 2,6,10-trimethyl-1,1-dimethoxy-3,5,9-undecantriene of Formula (12) in Different Conditions The crude product of 73.2 g of 4-methyl-5,5-dimethoxy-1-pentenyl-1-phosphoric acid diethyl ester of formula (10) of Examples 4-10 and 12.0 g of the residual crude product of Example 1 are combined together to obtain crude products, the total amount is 85.2 g, the total content is 92.7%, the crude products is used for the following experiment.

Using the same the method as Example 11, a certain amount of alkali and 20ml solvent (refer to Table 2) are added into a 250 ml a three necked flask under protection of nitrogen, and 20 ml solvent (refer to solvent of Table 2) dissolving a certain amount of 4-methyl-5,5-dimethoxy-1-pentenyl-1-phosphoric acid diethyl ester of formula (10) (refer to molar weight of Table 2) is dropped into the flask under magnetic stirring at a certain temperature (refer to temperature of Table 2) for half an hour, and continuously stirring for an hour to make a carbanion undergo dissociative reaction fully.

Then a solvent (refer to solvents of Table 2) dissolving 6.3 g of 6-methyl-5-heptene-2-one of formula (13) (0.05 mol, cis-trans isomers mixture) is dropped into the flask at a certain temperature of −30~25° C. for an hour, continuously stirring for half an hour at the same temperature, and determine the end of the reaction by tracking gas chromatography. 30 ml of water and 50 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residual material is evaporated at reduced pressure, the fraction within 97-101° C./1 mmHg is collected for measuring content of the crude product by GC analysis and yield. Results are shown in Table 2.

TABLE 2

Reactants, Reaction Temperatures And Reaction Results of The of Examples 14-19

| examples | alkali | amount of alkali (mole) | solvent | 4-methyl-5,5-dimethoxy-1-pentenyl-1-phosphoric acid diethyl ester (g, mole) | reaction temperature (°C.) | amount of Product (g) | GC content (%) | yield (%) |
|---|---|---|---|---|---|---|---|---|
| 14 | sodium ethoxide | 0.06 | toluene | 13.9, 0.050 | −20 | 6.3 | 86.2 | 43.1 |
| 15 | sodium tert-butoxide | 0.05 | glycol dimethyl ether | 12.5, 0.045 | −10 | 8.2 | 87.5 | 56.9 |
| 16 | n-butyl lithium | 0.051 | tetrahydro-furan/n-hexane | 13.0, 0.047 | −40 | 9.8 | 91.6 | 71.2 |
| 17 | potassium tert-butoxide | 0.063 | dimethyl sulfoxide | 17.4, 0.063 | 10 | 8.9 | 90.7 | 64.1 |
| 18 | potassium tert-butoxide | 0.0567 | dimethyl formamide | 15.6, 0.056 | 20 | 8.9 | 91.4 | 64.5 |
| 19 | potassium tert-butoxide | 0.046 | hexamethyl-phosphoric triamide | 11.6, 0.042 | 30 | 8.9 | 89.3 | 62.4 |

Note:
n-butyl lithium is 2.5 mol/l n-hexane solution thereof
Finally combine these crude products obtained to obtain 51 g crude product of 2,6,10-trimethyl-1,1- dimethoxy -3 ,5,9-undecantriene of formula (12) together with 80.2 g crude product of 2,6,10-trimethyl-1,1- dimethoxy -3,5,9-undecantriene of formula (12) of Examples 11, 12, 13 used for the following condensation reaction.tests, wherein their datum of ¹HNMR of Examples 14~19 are the same as that of Example 11.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A compound of 2,6,10-trimethyl-1,1-dialkoxy-3,5,9-undecan-triene of formula (12):

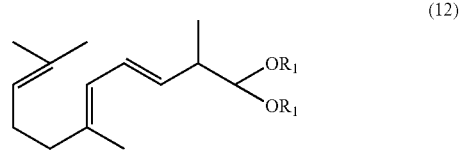

(12)

wherein $R_1$ is $C_{1-4}$ alkyl.

2. The 2,6,10-trimethyl-1,1-dialkoxy-3,5,9-undecantriene according to claim 1, characterized in that, the 2,6,10-trimethyl-1,1-dialkoxy-3,5,9-undecan-triene is 2,6,10-trimethyl-1,1-dimethoxy-3,5,9-undecan-triene.

3. A 4-methyl-5,5-dialkoxy-1-pentenyl-1-phosphoric acid dialkyl ester of formula (10):

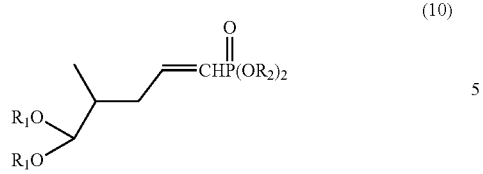

(10)

wherein $R_1$ and $R_2$ are $C_{1-4}$ alkyl.

4. The 4-methyl-5,5-dialkoxy-1-pentenyl-1-phosphoric acid dialkyl ester according to claim 3, characterized in that, the 4-methyl-5,5-dialkoxy-1-pentenyl-1-phosphoric acid dialkyl ester is 4-methyl-5,5-dimethoxy-1-pentenyl-1-phosphoric acid dimethyl ester, 4-methyl-5,5-dimethoxy-1-pentenyl-1-phosphoric acid diethyl ester or 4-methyl-5,5-dimethoxy-1-pentenyl-1-phosphoric acid diisopropyl ester.

* * * * *